United States Patent
Hägel

[11] Patent Number: 6,034,280
[45] Date of Patent: Mar. 7, 2000

[54] PROCESS FOR THE PRODUCTION OF 2,5-DIMETHYL-2,5-DI-T-BUTYLPEROXY-HEXANE

[75] Inventor: Eberhard Hägel, Icking, Germany

[73] Assignee: Peroxid-Chemie GmbH, Pullach, Germany

[21] Appl. No.: 09/171,233

[22] PCT Filed: Apr. 17, 1997

[86] PCT No.: PCT/EP97/01937

§ 371 Date: Oct. 13, 1998

§ 102(e) Date: Oct. 13, 1998

[87] PCT Pub. No.: WO97/38974

PCT Pub. Date: Oct. 23, 1997

[30] Foreign Application Priority Data

Apr. 17, 1996 [DE] Germany ............... 196 15 182

[51] Int. Cl.[7] ............................................. C07C 409/04
[52] U.S. Cl. ............................................. 568/561; 568/558
[58] Field of Search ................................. 568/558, 561

[56] References Cited

U.S. PATENT DOCUMENTS

| | | | |
|---|---|---|---|
| 3,086,966 | 4/1963 | Mageli | 525/387 |
| 3,135,805 | 6/1964 | Gilmont | 568/561 |
| 5,210,320 | 5/1993 | Tso | 568/561 |
| 5,371,298 | 12/1994 | Pourreau | 568/578 |

FOREIGN PATENT DOCUMENTS

| | | |
|---|---|---|
| 262639 | 4/1988 | European Pat. Off. . |
| 638551 | 2/1995 | European Pat. Off. . |
| 954361 | 4/1964 | United Kingdom . |

OTHER PUBLICATIONS

CA:73109099 abs of Tetrahedron by Kashiwagi 26 (15) pp. 3631–7 1970.
CA:106:42843 abs of J Organomet Chem. by Heidrich 312 (3) pp. 329–33 1986.
Cotton and Wilkinson "Advanced Inorganic Chemistry" textbook pp. 233–235 1972.

*Primary Examiner*—Gary Geist
*Assistant Examiner*—Jean F Vollano
*Attorney, Agent, or Firm*—Fulbright & Jaworski,LLP

[57] ABSTRACT

2,5-dimethyl-2,5-di-t-butylperoxy-hexane is produced by reacting 2,5-dimethyl-1,5-hexadiene with t-butylhydroperoxide under acid catalysis in the presence of an electron pair acceptor Lewis acid in a substantially anhydrous solvent. If one uses technical water-containing t-butylhydroperoxide, the water can be separated, after mixing with the 2,5-dimethyl-1,5-hexadiene, by adding sulfuric acid or calcium chloride and subsequently the electron pair acceptor Lewis acid is added.

7 Claims, No Drawings

PROCESS FOR THE PRODUCTION OF 2,5-DIMETHYL-2,5-DI-T-BUTYLPEROXY-HEXANE

This application is the national phase of PCT/EP97/01937 filed Apr. 17, 1997.

DESCRIPTION

The invention concerns a process for the production of 2,5-dimethyl-2,5-di-t-butylperoxy-hexane starting from 2,5 dimethyl-1,5-hexadiene and t-butylhydroperoxide.

2,5-dimethyl-2,5-di-t-butylperoxy-hexane (DHBP) is an important peroxide for cross-linking elastomers and thermoplastics and for the selective degradation of high molecular polypropylene.

The usual production process for DHBP starts with 2,5dimethyl-hexane-2,5-diol. This is reacted with hydrogen peroxide in a strong acidic medium to form the dihydroperoxide. The excess hydrogen peroxide is removed by suitable washing steps and the dihydroperoxide is further reacted with t-butanol also in a strong acidic medium to form DHBP.

The disadvantages of this two-step process are the poor yields (60–65% relative to the diol used), the long process times, the handling of the solid dihydroperoxide (critical compound with regard to safety) and the formation of large amounts of acidic liquid waste and wash solutions.

2,5-Dimethyl-hexane-2,5-diol cannot be reacted with t-butylhydroperoxide (TBHP) in acidic medium since the diol is very readily cyclysed to the 2,2,5,5-tetramethyltetrahydrofuran under the influence of acid.

The reaction of 2,5-dimethyl-1,5-hexadiene with TBHP using an acid catalyst is described in FR-PS 1 291 965. Perchloric acid, sulfuric acid, hydrogen chloride gas, toluenesulfonic acid and similar strong acids are listed as suitable acids. It is also mentioned that it is preferable to work in an anhydrous medium but 75% technical TBHP is also used in the examples. However, the reaction of 2,5-dimethyl-1,5-hexadiene with 75% TBHP and p-toluenesulfonic acid only results in a yield of 26% of DHBP. But even under anhydrous conditions high yields cannot be achieved with these stated acids. Furthermore the TBHP used in the FR-PS examples with a percentage of 98–99% is an extremely dangerous substance which can be neither produced nor handled on a technical scale. In addition large amounts of undesired by-products are formed in the reaction which can only be removed by distillative purification. This is an unacceptable process on an industrial scale for safety reasons.

There is therefore a need for a process which allows DHBP to be produced safely and environmentally-friendly with good yields and in short process cycles. The object of the invention was therefore to satisfy this need.

Surprisingly it was now found, and this is the basis of the invention, that in the presence of Lewis acids in a substantially anhydrous medium, DHBP can be obtained from 2,5-dimethyl-1,5-hexadiene and TBHP in short reaction times and in good yields and in satisfactory product quality.

The object defined above is therefore achieved according to the invention by a process for the production of 2,5-dimethyl-2,5-di-t-butylperoxy-hexane by reacting 2,5dimethyl-1,5-hexadiene with t-butylhydroperoxide under acid catalysis which is characterized in that the reaction is carried out in the presence of an electron pair acceptor Lewis acid in a substantially anhydrous solvent.

A major advantage of the invention from a safety standpoint is that anhydrous and thus hazardous TBHP does not have to be used, but rather that the water can be separated from the mixture of technical water-containing TBHP and 2,5-dimethyl-1,5-hexadiene by addition of relatively small amounts of dilute sulfuric acid or calcium chloride. The reaction to form DHBP then takes place after addition of the Lewis acid catalyst.

Suitable Lewis acids that can among others be used are:

Boron trifluoride etherate, zinc chloride ether complexes, anhydrous complexes of sulfuric acid with boric acid, phosphotungstic acid or lithium perchlorate or magnesium perchlorate in organic solvents such as e.g. ether.

The reaction is preferably carried out at a temperature of $-10°$ C. to $+50°$ C. and in particular in the range of $0°$ C. to $30°$ C.

TBHP can be used in a highly concentrated form. However, technical water-containing TBHP at a 60 to 80% concentration is preferred. TBHP is preferably used in a molar excess. For one mole of 2,5-dimethyl-1,5-hexadiene it is particularly preferable to use 2 to 6 moles TBHP, in particular 3 to 4 moles.

The Lewis acid catalyst is preferably used in amounts of 0.1 to 0.5 mole per mole 2,5-dimethyl-1,5-hexadiene although larger or smaller amounts can also be used depending on the respective Lewis acid and the process variables.

The process according to the invention avoids hazardous starting products and yields DHBP in yields of up to 90% of theory with a purity of over 80% with simple process measures and in particular without complicated or dangerous purification steps.

EXAMPLE 1

100 g 72% sulfuric acid is added to a mixture of 170 g (1.5 mol) 2,5-dimethyl-1,5-hexadiene and 600 g (5.25 mol) 78% TBHP while stirring and cooling, it is stirred for 5 minutes and the aqueous phase is separated (185 g). A further 35 g 72% sulfuric acid is added while stirring and cooling, it is stirred for 5 minutes and a further 47 g aqueous phase is separated.

While stirring and cooling a solution of 70 g (0.5 mol) boron trifluoride diethyl etherate in 50 ml ethyl acetate is added dropwise within ca. 35 minutes during which the temperature is allowed to increase to $30°$ C. and it is stirred for a further 3 hours at $30°$ C.

After addition of 400 ml water, the aqueous phase is separated. The product is washed twice with 15% sodium hydroxide solution and twice with water, dried with anhydrous sodium sulfate and filtered. After removing the volatile components by blowing out with air at $50°$ C., 282 g product with a DHBP content of 83% is obtained corresponding to a yield of 53.7% of theory.

EXAMPLE 2

The procedure is as in example 1 except that 140 ml (0.3 mol) of a 2.2 molar solution of a zinc chloride diethyl ether complex in methylene chloride is added as the catalyst and it is stirred for 2.5 hours at $40°$ C. After processing as in example 1, 308.6 g product is obtained with a DHBP content of 87% corresponding to a yield of 61.6% of theory.

EXAMPLE 3

The procedure is as in example 1 except that 50 ml (0.25 mol) of a 5 molar solution of lithium perchlorate in diethyl ether is added and it is stirred for 2 hours at 30° C. After processing as in example 1, 351 g product is obtained with a DHBP content of 91.7% corresponding to a yield of 73.9% of theory.

EXAMPLE 4

45 g 72% sulfuric acid is added to a mixture of 85 g (0.75 mol) 2,5-dimethyl-1,5-hexadiene and 260 g (2.25 mol) 78% TBHP while stirring and cooling, it is stirred for 5 minutes and the aqueous phase is separated (82 g). A further 15 g 72% sulfuric acid is added while stirring and cooling, it is stirred for 5 minutes and a further 22 g aqueous phase is separated.

While stirring and cooling a solution of 22.3 g (0.1 mol) anhydrous magnesium perchlorate in 40 g ethyl acetate is added dropwise within ca. 1 hour during which the temperature is kept below 20° C. It is stirred for a further 2 hours at 10 to 12° C., 300 ml water is added and the aqueous phase is separated. The organic phase is washed twice with 15% sodium hydroxide solution and twice with water. After removing the volatile components by blowing out with air at 50° C., 186 g product with a DHBP content of 94% is obtained corresponding to a yield of 80% of theory.

I claim:

1. A process for the production of 2,5-dimethyl-2,5-di-t-butylperoxy-hexane comprising reacting 2,5-dimethyl-1,5-hexadiene with t-butylhydroperoxide under acid catalysis in the presence of at least one electron pair acceptor Lewis acid selected from the group consisting of boron trifluoride etherate, zinc chloride-ether complex, anhydrous sulfuric acid-boric acid complex, lithium perchlorate, and magnesium perchlorate, said electron pair acceptor Lewis acid being present in an organic solvent in a substantially anhydrous solvent.

2. Process as claimed in claim 1, wherein the electron pair acceptor Lewis acid is used in an amount of 0.1 to 0.5 mole/mole 2,5-dimethyl-1,5hexadiene.

3. Process as claimed in claim 1, wherein 2 to 6 moles t-butylhydroperoxide per mole 2,5dimethyl-1,5-hexadiene is used.

4. Process as claimed in claim 3, wherein 3 to 4 moles t-butylhydroperoxide per mole 2,5dimethyl-1,5-hexadiene is used.

5. Process as claimed in claim 1, wherein the reaction is carried out at a temperature of −10 to +50° C.

6. Process as claimed in claim 1, wherein technical water-containing t-butylhydroperoxide is used and, after mixing with the 2,5-dimethyl-1,5hexadiene, the water is separated by addition of sulfuric acid or calcium chloride and subsequently the electron pair acceptor Lewis acid is added.

7. Process as claimed in claim 1, wherein the product phase is washed with water after completion of the reaction.

* * * * *